United States Patent [19]

Cuu

[11] Patent Number: 4,634,428
[45] Date of Patent: Jan. 6, 1987

[54] COVER FOR A DISPOSABLE SYRINGE

[76] Inventor: Cwo-Liang Cuu, Fl. 6-1, No. 149-15, Ho Ping 1st Rd., Kao Hsiung, Taiwan

[21] Appl. No.: 765,841

[22] Filed: Aug. 15, 1985

[51] Int. Cl.⁴ ............................................. A61M 5/00
[52] U.S. Cl. .................................... 604/110; 604/192
[58] Field of Search ............... 604/110, 192, 198, 263

[56] References Cited

U.S. PATENT DOCUMENTS

| | | | |
|---|---|---|---|
| 3,434,473 | 3/1969 | Smith | 604/192 |
| 3,597,582 | 8/1971 | Goode et al. | 604/110 |
| 3,712,302 | 1/1973 | Burke et al. | 604/110 |
| 3,747,812 | 7/1973 | Karman et al. | 604/110 |
| 3,796,359 | 3/1974 | Dick | 604/110 |
| 3,889,673 | 6/1975 | Dovey et al. | 604/192 |
| 3,893,608 | 7/1975 | Koenig | 604/110 |
| 4,266,544 | 5/1981 | Wardlaw | 604/110 |
| 4,273,123 | 6/1981 | Lemelson | 604/110 |

Primary Examiner—Stephen C. Pellegrino
Assistant Examiner—Michelle N. Lester
Attorney, Agent, or Firm—Kirschstein, Kirschstein, Ottinger & Israel

[57] ABSTRACT

A cover for a disposable syringe having a needle includes a cover body matchable with the syringe for covering therein the needle and a device, mounted in the cover body, for bending and retaining thereon the needle.

7 Claims, 8 Drawing Figures

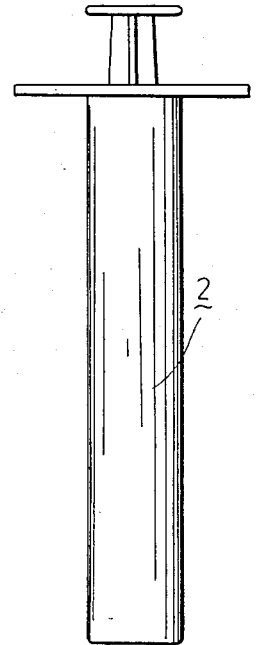
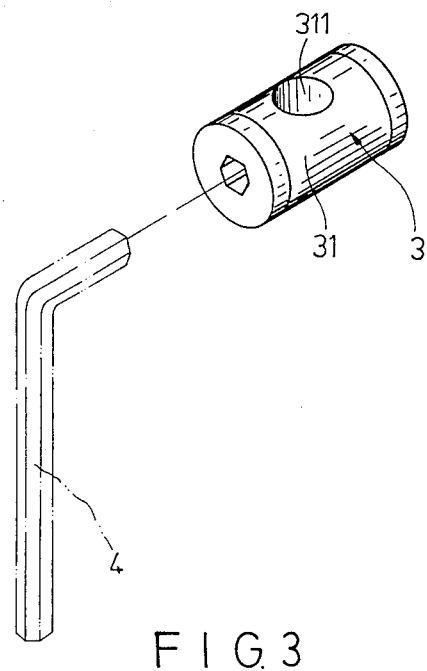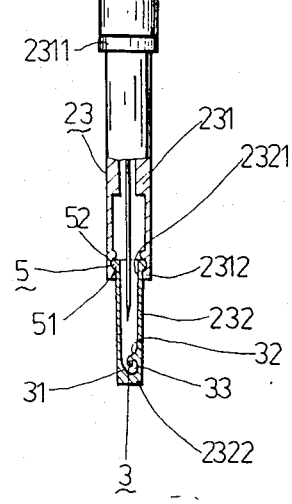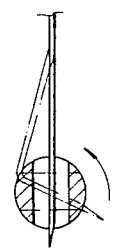
FIG. 5
FIG. 3
FIG. 4

COVER FOR A DISPOSABLE SYRINGE

BACKGROUND OF THE INVENTION

The present invention relates to a syringe, and more particularly to a cover for a disposable syringe.

The conventional glass syringe has been superseded by the disposable plastic syringe 11 as shown in FIG. 1, which includes a needle 12 and a cover 13 and is now mass produced, keeping costs low. However, it has been found by the applicant that the disposable plastic syringe is not, in fact, suitably disposed of. For example, the used syringe is picked up by children and used as a toy and is used by adults to act as a fuel-filling device, e.g. to fill a machine, e.g. a remote-controlled aircraft, with gasoline. Thus, the needle still can wound, and the syringe can still cause infection.

It is therefore attempted by the applicant to deal with the above situation.

SUMMARY OF THE INVENTION

It is therefore an object of the present invention to provide a disposable syringe which is rendered unusable after being used.

According to the present invention, a cover for a disposable syringe having a needle includes a cover body matchable with the syringe for covering therein the needle and means, mounted in the cover body, for bending and retaining thereon the needle.

Certainly, the bending and retaining means can include a rotatable column which, mounted on the cover body, has a central hole for the needle to pass through and will bend and retain thereon the needle when the syringe has been used and the column is rotated.

Certainly, the present cover can further include a tool, engagable with the column, for rotating the column.

Alternatively, the cover body of the present cover can include a first cover body having a first end matchable with the syringe and an opposite telescoping end and a second cover body having a second end telescopically engagable with the telescoping end and an opposite closed end.

Certainly, the bending and retaining means can be disposed on the closed end and the cover can further include an engaging means, disposed between the telescoping end and the second end, for temporarily fixing the telescoping end to the second end so that when the syringe is forced to have the second cover body telescoped into the first cover body and the second end escaped from the engaging means, the needle is bent and retained by the bending and retaining means.

Certainly, the bending and retaining means can include a curved surface, disposed in the closed end, for guiding the needle to be bent and a barb, rooted in the closed end, together with the inner wall of the closed end forming therebetween a room in which the portion of the needle which has been bent by the curved surface is received and retained.

Certainly, the engaging means can include a protrusion rimmed around the second end and a peripheral groove, provided around the inner wall of the telescoping end, for receiving thereon the protrusion.

Alternatively, the engaging means can include a plurality of protrusions separately disposed around the outer wall of the second end, a plurality of corresponding axial grooves, separately disposed around the inner surface of the telescoping end, for respectively sliding thereon the protrusions and a plurality of breakable barriers, respectively disposed on the grooves, for temporarily urging the protrusions against the bottom of the telescoping end.

Alternatively, the engaging means can include a plurality of protrusions separately disposed around the outer surface of the second end, a plurality of corresponding axial grooves, separately disposed around the inner wall of the telescoping end, for respectively sliding thereon the protrusions and a plurality of receiving spaces, separately disposed around the inner wall of the telescoping end and respectively communicating with the grooves near the bottom of the telescoping end, for respectively and temporarily receiving therein the protrusions so that when the second cover body is rotated to align the protrusions respectively with the grooves the second cover body can be forced to be telescoped in the first cover body to have the needle bent and retained by the bending and retaining means.

The present invention may best be understood with reference to the accompanying drawings, in which:

BRIEF DESCRIPTION OF THE DRAWING

FIG. 3 is a perspective view showing how a bending and retaining means of a cover in FIG. 2 can be rotated;

FIG. 4 is a schematic view showing a needle of a syringe after it has been bent by the bending and retaining means in FIG. 2;

FIG. 5 shows a second preferred embodiment of a cover according to the present invention;

DETAILED DESCRIPTION OF THE PREFERRED EMBODIMENT

Figure 1:
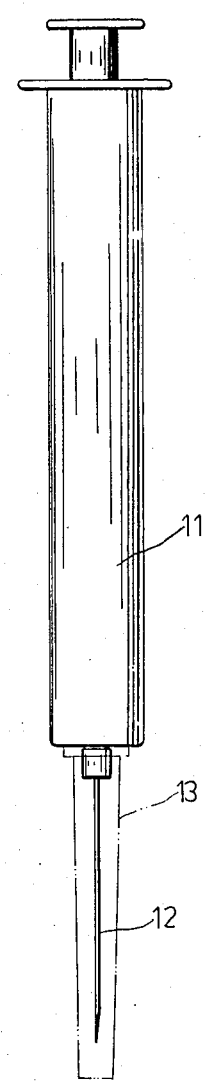
FIG. 1 is a schematic view showing a syringe incorporating a conventional cover.
Figure 2:
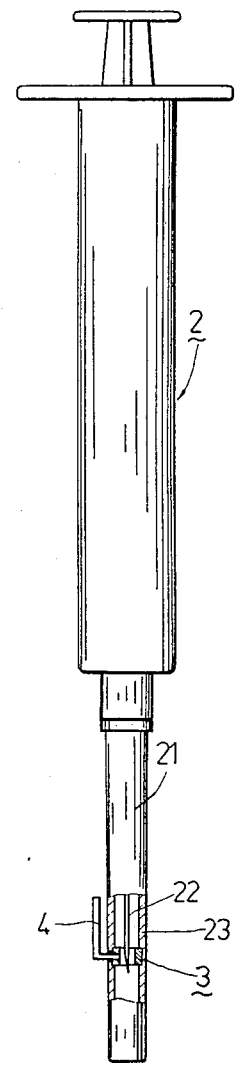
FIG. 2 shows a first preferred embodiment of a cover according to the present invention.

Referring now to FIGS. 2-4, there is shown the first preferred embodiment of a cover 21 according to the present invention for a disposable syringe 2 having a needle 22, which includes a cover body 23 matchable with syringe 2 for covering therein needle 22 and means 3, mounted in cover body 23, for bending and retaining thereon needle 22.

Bending and retaining means 3 is a rotatable column 31 which, mounted on cover body 23, has a central hole 311 for needle 22 to pass through and will bend and retain thereon needle 22 when syringe 2 has been used and column 31 is rotated. A tool 4, engagable with column 31, can be provided for rotating column 31.

Figure 6:
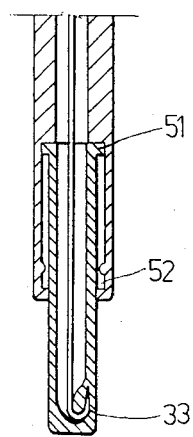
FIG. 6 is a schematic view showing a needle of a syringe after it has been bent by the bending and retaining means in FIG. 5.

As shown in FIGS. 5 and 6, there is shown a second preferred embodiment of the present cover 21. Cover body 23 includes a first cover body 231 having a first end 2311 matchable with syringe 2 and an opposite telescoping end 2312 and a second cover body 232 having a second end 2321 telescopically engagable with telescoping end 2312 and an opposite closed end 2322 on which bending and retaining means 3 is disposed. Between telescoping end 2312 and second end 2321, there is disposed an engaging means 5 for temporarily fixing telescoping end 2312 to second end 2321 so that when syringe 2 is forced to have second cover body 231 telescoped into first cover body 232 and second end 2321 escaped from engaging means 5, needle 22 is bent and retained by the means 3 which includes a curved surface 31, disposed in closed end 2322, for guiding needle 22 to be bent and a barb 32, rooted in closed end 2322, together with the inner wall of closed end 2322 forming therebetween a room 33 in which the portion of needle 22 which has been bent by curved surface 31 is received and retained. Engaging means 5 can include a protrusion 51 rimmed around second end 2321 and a peripheral groove 52, provided around the inner wall of telescoping end 2312, for receiving thereon protrusion 51.

Figure 7:
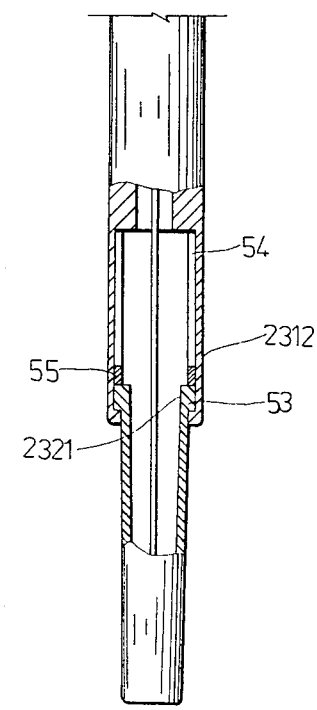
FIG. 7 shows a third preferred embodiment of a cover according to the present invention.

As shown in FIG. 7, engaging means 5 can alternatively include a plurality of protrusions 53 separately disposed around the outer wall of second end 2321, a plurality of corresponding axial grooves 54, separately disposed around the inner surface of telescoping end 2312, for respectively sliding thereon protrusions 53 and a plurality of breakable obstacles 55, respectively disposed on grooves 54, for temporarily urging protrusions 53 against the bottom of telescoping end 2312.

Figure 8:
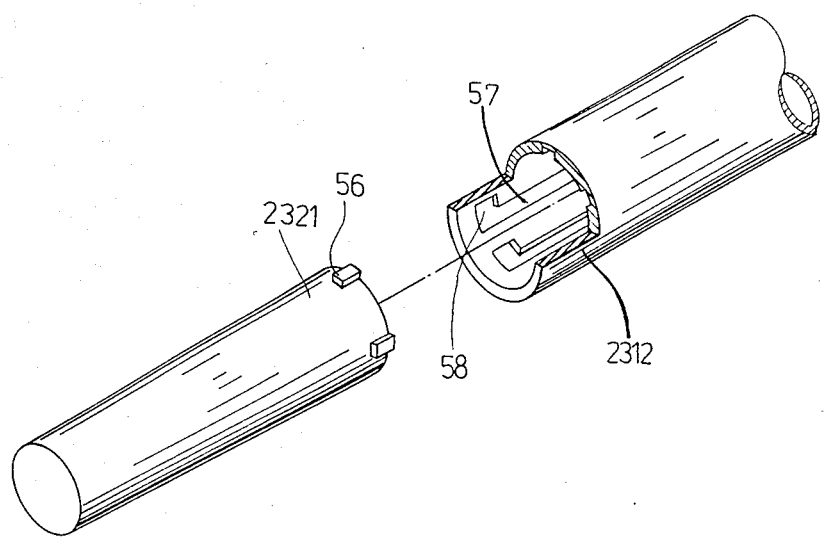
FIG. 8 shows a fourth preferred embodiment of a cover according to the present invention.

Alternatively, as shown in FIG. 8, engaging means 5 can include a plurality of protrusions 56 separately disposed around the outer surface of second end 2321, a plurality of corresponding axial grooves 57, separately disposed around the inner wall of telescoping end 2312, for respectively sliding thereon protrusions 56 and a plurality of receiving spaces 58, separately disposed around the inner wall of telescoping end 2312 and respectively communicating with grooves 57 near the bottom of telescoping end 2312, for respectively and temporarily receiving therein protrusions 56 so that when second cover body 232 is rotated to align protrusions 56 respectively with grooves 57, second cover body 232 can be forced to be telescoped in first cover body 231 to have needle 22 bent and retained by bending and retaining means 3.

While the present invention has been described in connection with what is presently considered to be the most practical and preferred embodiments, it is to be understood that the present invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

What I claim is:

1. A cover for destroying a needle on a disposable syringe after use, comprising:
   (a) a pair of tubular cover members, each being elongated in an axial direction lengthwise of the needle and bounding interiors in which the needle is enclosed;
   (b) one of the cover members being stationarily mounted on the syringe;
   (c) the other of the cover members being movably mounted on the one cover member for telescoping movement along the axial direction between extended and retracted positions in which the cover members axially overlap each other over a lesser and a greater distance respectively;
   (d) means for releasably holding the cover members in the extended position prior to use of the syringe to protect the needle; and
   (e) destroying means on the other cover member for bending the needle during said telescoping movement, and for retaining the needle within the other cover member even after said telescoping movement.

2. The cover as recited in claim 1, wherein the destroying means includes guiding means in the interior of the other cover member and jointly movable therewith, for forceably guiding the needle along a curved guide surface into a deformed, bent shape during said telescoping movement.

3. The cover as recited in claim 2, wherein the other cover member has a closed axial end wall whose interior face, which faces a tip of the needle, is at least partly constituted by the curved guide surface.

4. The cover as recited in claim 3, wherein the guiding means includes a bulbous lip within the interior of the other cover member and, together with the curved guide surface, bounding an arcuate chamber in which the tip of the bent needle is retained.

5. The cover as recited in claim 1, wherein the holding means includes an annular rim on the other cover member, and an annular groove on the one cover member, said rim being yieldingly received within the groove in the extended position.

6. The cover as recited in claim 1, wherein the holding means includes a plurality of radially-extending protrusions on the other cover member, a plurality of axially-extending channels on the one cover member, a plurality of barriers located within the channels and engaging the protrusions to position the cover members in the extended position, said barriers being breakable in response to said telescoping movement to permit the protrusions to be moved along and within the channels.

7. The cover as recited in claim 1, wherein the holding means includes a plurality of radially-extending protrusions on the other cover member, a plurality of axially-extending channels on the one cover member, and a plurality of receiving spaces each communicating with a respective channel and extending at least partially in a circumferential direction, each protrusion being received in a respective receiving space in the extended position and being moved circumferentially along the respective receiving space in response to circumferential turning to a respective channel along and within which the respective protrusion is moved axially during said telescoping movement.

* * * * *